United States Patent [19]

Uhm et al.

[11] Patent Number: 4,675,434
[45] Date of Patent: Jun. 23, 1987

[54] PROCESS FOR PRODUCING PHTHALIC ACID ESTERS

[75] Inventors: Sung J. Uhm; Tae J. Lee; Eun S. Choi; Dong W. Yu, all of Seoul, Rep. of Korea

[73] Assignee: Korea Advanced Institute of Science & Technology, Seoul, Rep. of Korea

[21] Appl. No.: 671,921

[22] Filed: Nov. 15, 1984

[30] Foreign Application Priority Data

Nov. 30, 1983 [KR] Rep. of Korea ................. 5646/1983

[51] Int. Cl.$^4$ ............................................. C07C 67/08
[52] U.S. Cl. ...................................... 560/99; 556/106; 560/85; 560/89
[58] Field of Search ...................... 560/99; 260/429.7; 556/85, 89

[56] References Cited

U.S. PATENT DOCUMENTS 3,332,983 7/1967 Barie et al. ............................. 560/99
3,341,570 9/1967 Barie ..................................... 560/99

FOREIGN PATENT DOCUMENTS 3244752 6/1984 Fed. Rep. of Germany .
810381 3/1959 United Kingdom .

OTHER PUBLICATIONS

Seyforth et al, *J.A.C.S.*, 79: pp. 515–517, (1957).
Anderson, *Inorganic Chemistry*, 3: pp. 108–109, (1964).
Yeats et al, *Inorganic Chemistry*, vol. 11, No. 11, pp. 2634–2641, (1972).

*Primary Examiner*—Natalie Trousof
*Assistant Examiner*—Vera C. Clarke
*Attorney, Agent, or Firm*—Birch, Stewart, Kolasch & Birch

[57] ABSTRACT

A process for preparing phthalic acid esters of formula (I) which comprises reacting the phthalic acids of formula (II) with an aliphatic alcohol in the presence of a catalyst consisting essentially of the dialkyltinoxides of formula (III):

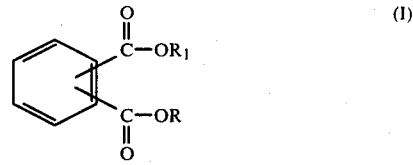

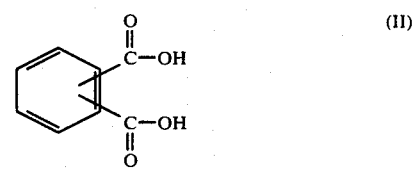

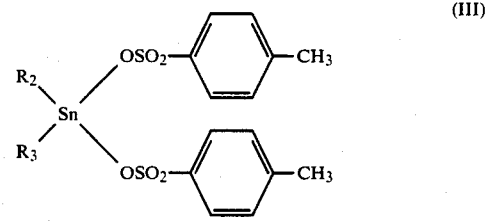

wherein R and $R_1$ are the same or different and include both straight and branch chain aliphatic alkyl groups containing 4 to 13 carbon atoms and $R_2$ and $R_3$ are straight or branch chain aliphatic alkyl groups containing 1 to 8 carbon atoms.

11 Claims, No Drawings

PROCESS FOR PRODUCING PHTHALIC ACID ESTERS

BACKGROUND OF THE INVENTION

The present invention relates to a process for producing phthalic acid esters. More particularly, the present invention pertains to a new and improved process for the preparation of phthalic acid esters of the following formula (I) in high yield:

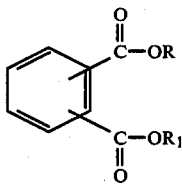

wherein R and $R_1$ each is a straight or branch chain aliphatic alkyl group containing 4 to 13 carbon atoms and R and $R_1$ are the same or different from each other. The esters are made from phthalic acids of the following formula (II):

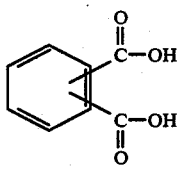

which are reacted with aliphatic alcohols in the presence of a catalyst.

In the above formulas (I) and (II), the various groups are positioned on the ring either ortho, meta or para with respect to each other.

The phthalic acid esters of the present invention are useful with polymeric materials, particularly as plasticizers for PVC. The dioctylphthalate of the phthalic acid esters of the present invention is particularly useful as an additive for inks, paints, adhesives and the like. When used in this capacity it is present in an amount of up to about 40% by weight. The plasticizers of the present invention improve the physical properties of the polymers, such as the heat resistance, cold resistance, and electronic activity of the polymers simultaneously with low volatility or processing activity.

Various processes for the preparation of phthalic acid esters are known in the art. Specific examples of such processes are as follows:

(1) A process for the preparation of phthalic acid esters wherein the catalyst which is utilized is sulfuric acid for reducing corrosion and production costs. This process, however, has a number of disadvantages. Thus, by-products such as ethers or olefins are produced by the dehydration of the alcohols when the concentration of the sulfuric acid is increased or the reaction temperature becomes elevated.

Furthermore, there are the disadvantages of a low yield and a dark colored product which is more than 7 times the color density of the phthalic esters. It is also described in this process that high reaction speed, high yield and low color density can be obtained using metal catalysts such as alumina, tin, lead and zinc. However, utilizing these catalysts creates an energy problem because the reaction temperature has to be elevated higher than the boiling point of the alcohols and it takes about 7 hours to complete the reaction.

(2) The Encyclopedia of Chemical Technology Interscience, New York, 1965 discloses a process for producing phthalic acid esters in the presence of an organic compound catalyst such as titanium or zirconium. However, this process will be difficult to industrialize because of the high catalyst cost and the difficulty in its recovery.

(3) British Pat. No. 1,061,172 discloses a process for the production of carboxylic acid esters which have been catalyzed by titanium peroxide, for example, hydrated or partially hydrated titanium peroxides. Advantages such as a high yield, a short reaction time, good color density and multiple use of the catalyst are features of this process. However, this process cannot be industrialized because of the high cost of the catalyst.

(4) French Pat. No. 1,529,507 discloses a process for the production of phthalic acid esters without the use of a catalyst to eliminate the neutralization and washing steps. This patent, however, has the disadvantages of high equipment costs and high power requirements when using three stage reactors at high temperatures of 210°, 215° and 220° C.

All of the prior art processes described above are limited to the orthodioctylphthalate, in contrast to the present invention.

Recently, improvements have been made in this process of esterification for eliminating or resolving the disadvantages or problems noted hereinabove. Thus, the process has been divided into the 5 steps of reaction neutralization, washing, alcohol recovery, reduced pressure distillation and discoloration. However, a large amount of time is required for the neutralization and wash step after the reaction is completed which is the reason why sulfuric acid or para-toluene sulfuric acid is used as the catalyst. Recently, an organic tin compound has been used as the catalyst in order to eliminate the neutralization step. However, this catalyst has the disadvantages of a high reaction temperature, cloudy color, high acidity of the product and the high cost of equipment and power. Accordingly, it is desirable to develop an improved process for producing phthalic acid esters in excellent yield utilizing low reaction temperatures, and eliminating the need of a neutralization or wash step with easy catalyst recovery.

OBJECTS AND SUMMARY OF THE INVENTION

Accordingly, it is therefore an object of the present invention to provide an improved process for the production of phthalic acid esters in high yield.

Another object of the present invention is to provide an improved process for preparing phthalic acid esters by utilizing a dialkyltinoxide catalyst.

Yet aother object of the present invention is to provide an improved process for preparing phthalic acid esters by utilizing a catalyst which is stable at the high temperatures of reduced distillation.

Still another object of the present invention is to provide an improved process for preparing phthalic acid estrs which eliminates the neutralization or wash steps, substantially eliminates energy expenses for disposed water and simplifies the catalyst separation step.

A further object of the present invention is to provide an improved process for the production of phthalic acid esters having a transparent color.

Other objects and further scope of applicability of the present invention will become apparent from the detailed description given hereinafter. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

The present invention provides an economical process for the production of phthalic acid esters, utilizing new dialkyltinoxides as the catalyst in the esterification reaction of phthalic acids and aliphatic alcohol.

The process for making the new dialkyltinoxides is as follows. 1 mole of dialkyltinoxide of the following formula (III):

(III)

wherein $R_2$ and $R_3$ are each a straight or branched chain aliphatic alkyl group containing 1 to 8 carbon atoms, and 2 moles of para-toluene sulfuric acid and benzene or toluene are continuously introduced into a reactor and heated at 120° C. with agitation. The water produced during the reaction is eliminted by the benzene or toluene and the benzene or toluene is removed. A white recrystallized product of the following formula (IV) is produced:

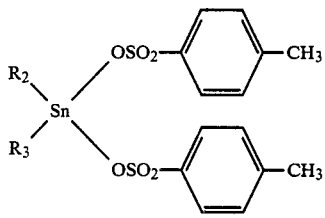

(IV)

wherein $R_2$ and $R_3$ are the same as defined above.

According to a preferred embodiment of the present invention, phthalic acid esters of Formula (I) in a 99% yield are prepared by reacting 1 mole of phthalic acid (II) with 4 moles of an aliphatic alcohol, for example, octylalcohol in presence of about 0.1-1.0 weight percent of the dialkyltinoxide catalyst of Formula (IV) at about 140°-220° C. with agitation for up to 7 hours. Preferably, the reacting temperature is about 180°-220° C. and the reaction is conducted for about 4 hours at ambient pressure. After the reaction is completed, the alcohol can be recovered by distillation for reuse at a reduced pressure of 0.2 torr. and a temperature of 210° C. However, the catalyst, because of its stability, is not adversely affected by the high temperature.

Gas chromatography having a SE-30 filler and neutralization titration is used to determine the yield. Also an infrared gas analyzer, nuclear magnetic resonance, thin layer chromatography and liquid chromatography can also be used for this purpose.

In the present invention, in order to confirm the presence of the phthalic acid esters, the length of time the esters are in the gas chromatographic device are measured with the following results: Ortho-phthalate is 29.3 mn; meta-phthalate is 30.5 mn and para-phthalate is 32.1 mn.

In thin layer chromatography using diethylether, the value of Rf for ortho-phthalate is 0.81, for meta-phthalate is 0.83 and for para-phthalate is 0.87.

It is confirmed that the products produced by utilizing either test procedure is substantially the same. Also, the ester characteristics peak at 1710 cm[31 1] when using the techniques of infrared gas analysis or nuclear magnetic resonance.

The reaction scheme of the present invention is as follows:

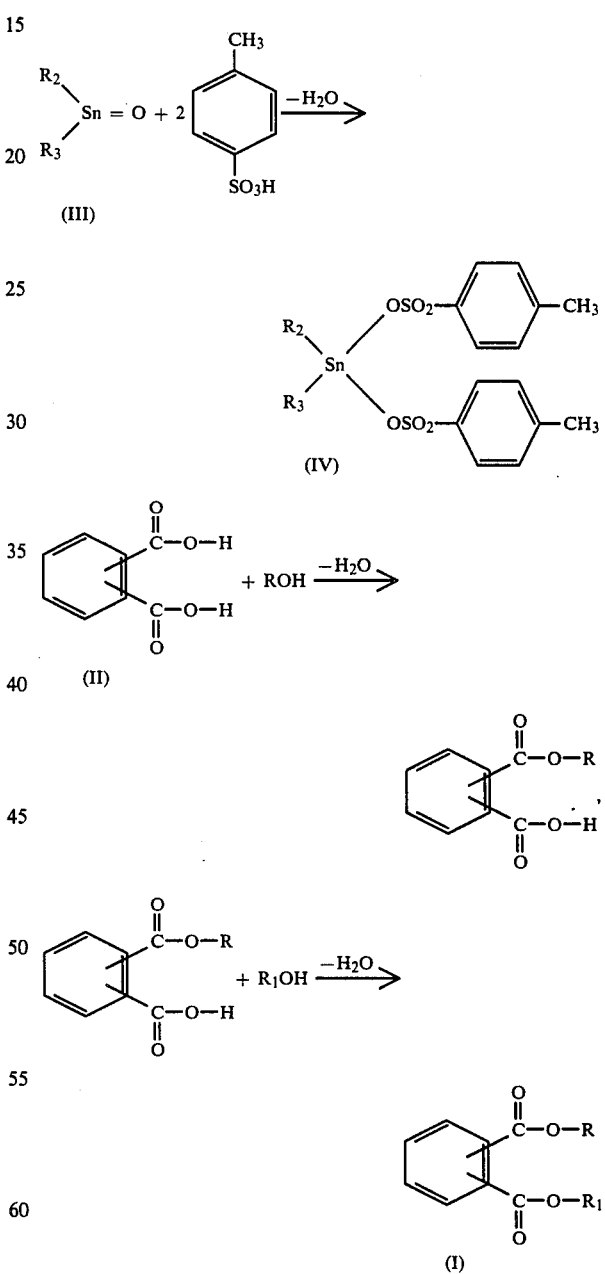

wherein R, R1, R2 and R3 are the same as defined above.

The following examples more specifically illustrate the present invention, but should not be considered as limiting the scope thereof.

EXAMPLE 1

A 1,000 cc round flask is charged with 50 g (0.3M) of terephthalic acid, 156.2 g (1.2M) of octyl alcohol and 0.5 g (1 weight percent) of dibutyltinoxide. The mixture is stirred and simulstaneously heated for 4 hours at 180° C., which is the boiling point of the octyl alcohol at normal pressure. While the reaction is proceeding, the produced water is continuously removed and dry nitrogen gas is blown into the reactor so as to intercept the moisture in air. During the reaction a sample is frequently removed for analysis. After the reaction is completed, the reaction mixture is distillated under reduced pressure and 116 g of dioctylphthalate representing a yield of 99% is obtained. The residence time in the gas chromatographic device is 32.1 min and the Rf value is 0.87 thereby confirming that the final product is dioctylphthalate. The analysis shows that there are no by-products such as olefins produced in the process.

EXAMPLE 2

The procedure of Example 1 is followed utilizing the catalysts shown in Table 1. The yields are also shown in Table 1.

TABLE 1

| alkyl group ($R_2 = R_3$) of the catalyst | conversion ratio | yield (%) |
| --- | --- | --- |
| methyl | 100 | 98.2 |
| propyl | 100 | 98.3 |
| butyl | 100 | 99.0 |
| hexyl | 99.0 | 98.6 |
| octyl | 98.2 | 98.0 |

As can be seen, the yield does not rely on the alkyl radical of the catalyst and accordingly the activity of the catalyst depends on the reactivated radical of the organic acid.

EXAMPLE 3

Utilizing the same materials as in Example 1 but changing the mole ratio of the telephthalic acid and the alcohols, the yield and conversion ratio of the resulting products are shown in Table 2 below.

TABLE 2

| mole ratio (telephthalic-acid:alcohol) | conversion ratio | yield (%) |
| --- | --- | --- |
| 1:2.05 | 75 | 74.2 |
| 1:2.2 | 82 | 81.5 |
| 1:2.5 | 89 | 88.4 |
| 1:3.0 | 95 | 94.6 |
| 1:3.5 | 99.8 | 99.5 |
| 1:4.0 | 100.0 | 99.0 |

EXAMPLE 4

Using the same material as in Example 1, but changing the reaction temperature, the yield of the products are shown in Table 3 below.

TABLE 3

| reaction temperature (°C.) | conversion ratio | yield (%) |
| --- | --- | --- |
| 140 | 60 | 59.9 |
| 150 | 73 | 72.8 |
| 160 | 84 | 83.0 |
| 170 | 95 | 93.6 |

TABLE 3-continued

| reaction temperature (°C.) | conversion ratio | yield (%) |
| --- | --- | --- |
| 180 | 100 | 98.0 |

EXAMPLE 5

Following the same procedure of Example 1, the reaction is performed many times, using the catalyst residue which is obtained by distilling the used catalyst under reduced pressure to achieve the product recovery as shown in Table 4 below.

TABLE 4

| reaction times | conversion ratio | yield (%) |
| --- | --- | --- |
| 1 | 100 | 99.0 |
| 2 | 100 | 99.0 |
| 5 | 99.0 | 96.8 |
| 8 | 98.0 | 95.0 |
| 10 | 98.0 | 95.0 |

EXAMPLE 6

Using the same materials as in Example 1 but changing the alcohol, the conversion ratio and yield of final prdoucts are shown in Table 5 below.

TABLE 5

| kind of alcohol | conversion ration | yield (%) |
| --- | --- | --- |
| iso-butanol | 100 | 98.4 |
| cyclohexanol | 100 | 98.2 |
| n-octanol | 98 | 97.8 |
| n-nonanol | 97 | 96.3 |
| n-decanol | 96 | 94.8 |
| n-dodecanol | 93 | 92.1 |

EXAMPLE 7

The procedure of Example 1 was followed utilizing the same amount (0.3M) of ortho- and meta-phthalic acid instead of telephthalic acid. The results are shown in Table 6 below.

TABLE 6

| kinds of acid | conversion ratio | yield (%) |
| --- | --- | --- |
| anhydrous phthalic acid | 97 | 89 |
| isophthalic acid | 98 | 92.5 |

From Table 6 it is supposed that the reason for the low yield of anhydrous phthalic acid or isophthalic acid is the simultaneous formation of some monosubstituted esters.

EXAMPLE 8

Using anhydrous phthalic acid and the same reaction conditions of Example 1 with the exception that an elevated reaction temperature is utilized, the following results are obtained.

TABLE 7

| reaction temperature (°C.) | conversion ratio | yield (%) |
| --- | --- | --- |
| 190 | 98 | 95.0 |
| 200 | 99.5 | 96.5 |
| 210 | 100 | 97.4 |

TABLE 7-continued

| | | |
|---|---|---|
| 220 | 100 | 99.1 |

EXAMPLE 9

The procedure of Example 1 is followed but different catalyst are utilized. The results are shown in Table 8.

TABLE 8

| catalyst | reaction period (hr) | conversion ratio | yield (%) |
|---|---|---|---|
| sulfuric acid | 5 | 100 | 80 |
| para-toluene sulfuric acid | 6 | 100 | 87 |
| dibutyltin-oxide | 9 | 100 | 99.8 |
| aluminum sulfoxide | 8 | 100 | 96.5 |

The invention being thus described, it will be obvious that the same may be varied in many ways. Such variations are not to be regarded as a departure from the spirit and scope of the invention, and all such modifications as would be obvious to one skilled in the art are intended to be included in the scope of the following claims.

What is claimed is:

1. A process for preparing phthalic acid esters of formula (I) which comprises reacting the phthalic acids of formula (II) with an aliphatic alcohol in the presence of a catalyst consisting essentially of the diakyltinoxides of formula (IV):

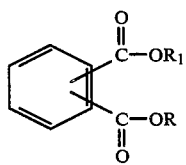

(I)

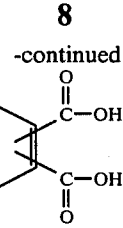

(II)

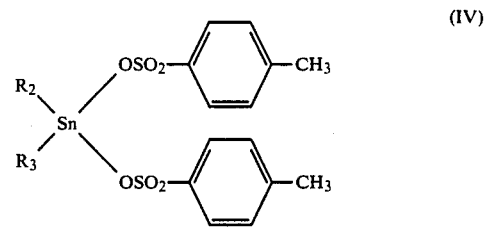

(IV)

wherein R and $R_1$ are the same or different and include both straight and branch chain aliphatic alkyl groups containing 4 to 13 carbon atoms and $R_2$ and $R_3$ are straight or branch chain aliphatic alkyl groups containing 1 to 8 carbon atoms.

2. The process of preparing the phthalic acid esters of claim 1, wherein the reaction is conducted at a temperature of about 160° to 180° C.

3. The process for preparing the phthalic acid esters of claim 1, wherein the reaction period is from 4 to 9 hours.

4. The process for preparing the phthalic acid esters of claim 1, wherein the phthalic acids are ortho-, meta-, and/or para-phthalic carboxylic acids.

5. The process for preparing the phthalic acid esters of claim 1, wherein the phthalic acid esters are ortho-, meta-, and/or para-phthalic acid esters.

6. The process for preparing the phthalic acid esters of claim 1, wherein the catalyst is dibutyltin-bis-(p-toylysulfonate.

7. The process for preparing phthalic acid esters of claim 1, wherein the mole ratio of the phthalic acid to the aliphatic alcohol varies from 1:3.0 to 1:4.0.

8. The process of claim 7, wherein the mole ratio of the phthalic acid to the aliphatic alcohol is 1:4.

9. The process for preparing phthalic acid esters of claim 1, wherein the catalyst is present in an amount of about 0.1 to 1.0 percent by weight.

10. The process for preparing phthalic acid esters of claim 1, wherein the reaction is conducted at a temperature of about 140° to 220° C.

11. The process for preparing phthalic acid esters of claim 3, wherein the reaction period is about 7 hours.

* * * * *